United States Patent [19]

Coons

[11] Patent Number: 4,693,250
[45] Date of Patent: Sep. 15, 1987

[54] METHOD FOR DILATING PUNCTURE SITE IN THE RENAL PELVIS

[75] Inventor: Harold G. Coons, San Diego, Calif.

[73] Assignee: Cook, Incorporated, Bloomington, Ind.

[21] Appl. No.: 823,767

[22] Filed: Jan. 29, 1986

[51] Int. Cl.$^4$ ............................................ A61M 29/00
[52] U.S. Cl. ........................................ 128/345; 604/106
[58] Field of Search ................. 128/17, 18, 345, 341, 128/343, 321, 322, 303.11; 604/105, 106

[56] References Cited

U.S. PATENT DOCUMENTS

| | | | |
|---|---|---|---|
| 474,130 | 5/1892 | Henger | 128/322 |
| 673,598 | 5/1901 | Dolge | 128/345 X |
| 762,743 | 6/1904 | McDade | 128/17 |
| 1,097,978 | 5/1914 | Johnson | 128/345 |
| 1,328,624 | 1/1920 | Graham | 128/345 |
| 1,340,501 | 5/1920 | Roberts | 128/321 |
| 1,592,836 | 7/1926 | Moench | 128/356 |
| 3,143,114 | 8/1964 | McCarthy et al. | 128/345 X |
| 3,446,211 | 5/1969 | Markham | 128/322 |
| 4,034,746 | 7/1977 | Williams | 128/17 |
| 4,449,532 | 5/1984 | Storz | 128/341 |

FOREIGN PATENT DOCUMENTS 36108 2/1906 Switzerland .................... 128/345

Primary Examiner—Michael H. Thaler
Attorney, Agent, or Firm—Woodard, Weikart, Emhardt & Naughton

[57] ABSTRACT

A renal tissue puncture site dilator with grooves in the jaws to receive a wire guide. The renal tissue dilator is a scissor-like surgical instrument, similar to a clamp, with jaws that have a triangular cross section to aid in tearing of tissue. The grooves in the jaws form a channel beginning at the tips of the jaws and exiting the jaws through the side of the jaws. This channel has a circular cross section, designed to slidably receive a wire guide. A needle is inserted into the renal tissue and a wire guide is threaded into the needle. The needle is removed. The instrument is threaded onto the wire guide and moved into the puncture site. The puncture site is dilated by opening the jaws of the clamp thereby tearing the renal tissue. The dilated tissue may be further dilated by rotating the clamp approximately 90° and again opening the jaws of the clamp to tear the renal tissue further. The turning of the clamp and opening of the jaws to enlarge the puncture in renal tissue is continued until an opening of appropriate size is obtained.

9 Claims, 5 Drawing Figures

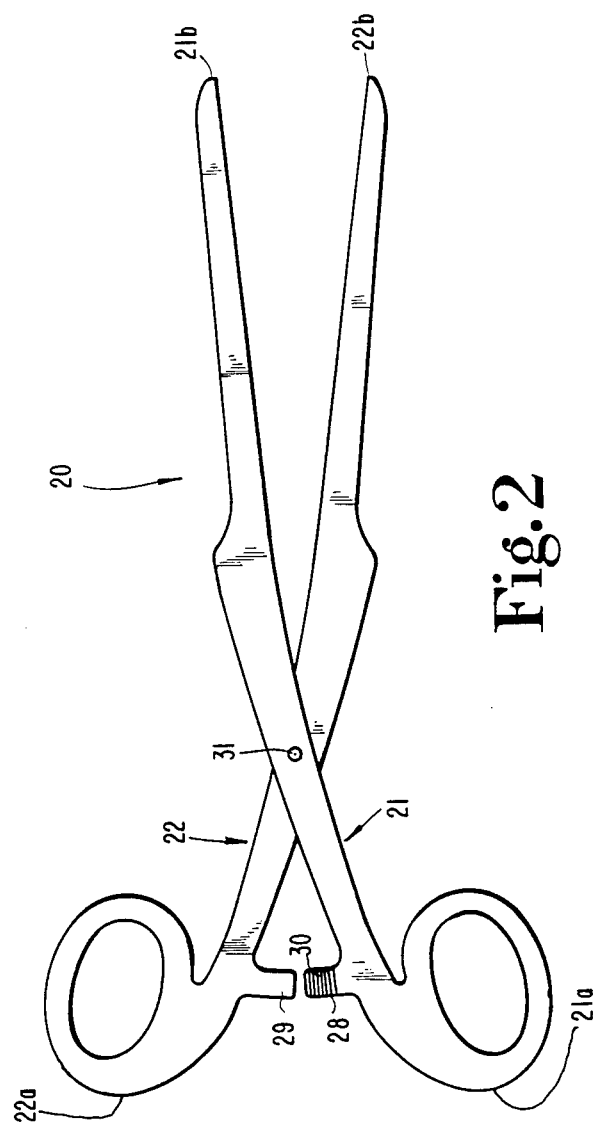

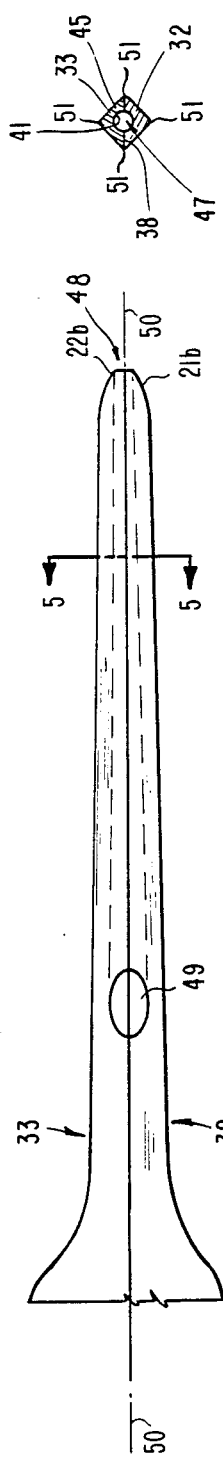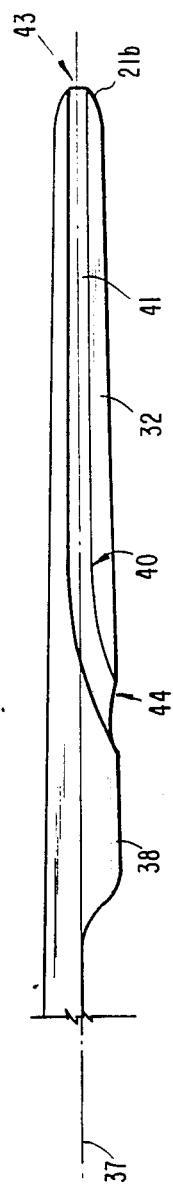

METHOD FOR DILATING PUNCTURE SITE IN THE RENAL PELVIS

BACKGROUND OF THE INVENTION

This invention relates to the field of medical and surgical techniques and instruments, and more particularly to a method for the dilation of a puncture site in fascial tissue or a nephrostomy tract dilation.

In the current practice, puncture sites in the renal pelvis are dilated with tapered tubes of progressively larger sizes until the desired size is reached. The main difficulty with such an approach is the penetration of the ileo-lumbar fascia at the kidney. This fascia is a layer of strong fibrous tissue that is very difficult to dilate. As the tapered dilators enter such a layer, considerable axial force is required to penetrate. This force results in pain for the patient and the increased risk of damage to surrounding tissue. The present device does not use axial force to dilate tissue perpendicular to the puncture axis. Instead, the device consists of a modified long-nosed surgical clamp. The jaws of the clamp are hollowed out so that they can be inserted initially over a wire guide similar to a regular dilator. Once the tip ends of the clamp are through the fascia and into the renal pelvis, the clamp is opened by forcing the jaws to spread apart, thus tearing the fascial tissue and enlarging the puncture. The clamp is then closed, rotated 90% or so and then the process is repeated. This is continued until the opening to the fascial material is large enough to accept whatever device the physician plans to use next.

Many variations and types of surgical instruments have appeared and representative examples of these variations and types are disclosed by the following group of patent references. Each reference pertains in one way or another to surgical instruments, though some references are believed to be more relevant to the present invention than others.

| Patent No. | Patentee |
| --- | --- |
| 474,130 | Henger |
| 1,592,836 | Moench |
| 1,340,501 | Roberts |
| 762,743 | McDade |
| 3,446,211 | Markham |
| 4,034,746 | Williams |
| 4,449,532 | Storz |
| 1,097,978 | Johnson |

Henger discloses a surgical instrument designed to be taken apart and reunited in the simplest manner to allow for thorough cleaning and sharpening. Henger is relevant to the present invention only in that an instrument similar to that illustrated in FIGS. 1 through 5 may be modified to satisfy the present invention. Modification would be required because the instruments disclosed in Henger have no wire guide channel.

Moench discloses a surgical instrument for removal of small objects from the nasal, auricular or other cavities. FIGS. 1 and 3 disclose a rod or shank 10 which is made of wire and slides within a channel and tube 11. Shank 10 and tube 11 operate to grip a small object. The relevance of Moench is limited to the disclosure of an instrument in which a wire is slidably inserted in a channel. It should be noted that shank 10 is not a guide for tube 11, but instead tube 11 protects shank 10 to allow it to be inserted into a cavity. Also it is apparent from Moench that the instrument disclosed therein can't be opened for tearing of tissue.

Roberts discloses a surgical appliance adapted for tying knots in ligatures in cavities where it is difficult or impossible to reach with the hands. FIGS. 2 and 3 disclose grooves 11 in the non-adjacent sides of jaws 5. Grooves 11 extend longitudinally along jaws 5 but are inclined with respect to the axis of the jaw to provide an opening at the side of the jaw. The grooves 11 and openings are for insertion of ligatures therethrough. The relevance of Roberts is limited to the disclosure of an instrument with side-ports and grooves for holding tubular material. It should be noted that the grooves in Roberts are not in adjacent sides of the jaws to form a channel for receiving a wire guide and cross-sections of the jaws are not designed to accommodate tearing of tissue.

McDade discloses a cervical director for use with an applicator in introducing material into the uterus. FIGS. 1 and 2 disclose curved blades 3 and 3a which are hingedly attached to one another so that they may be forced apart when gauze is inserted therethrough. The relevance of McDade is limited to the disclosure of an instrument which has a channel for slidably receiving material. The McDade device clearly is not adopted for tearing tissue with the jaws when the handles of the instrument are moved apart as McDade discloses only a single handle and no pair of handles.

Markham discloses a surgical clamp. FIGS. 1 and 7 through 9 disclose a clamp with longitudinally extending recesses. The relevance of Markham is limited to the disclosure of an instrument with a longitudinally extending recesses. The device disclosed in Markham may be modified to satisfy the teachings of the present invention, but the device does not, as disclosed, teach the present invention.

Williams discloses a surgical retractor. The only relevance of the instrument disclosed in Williams is that it is designed to spread or increase the width across an incision.

Storz discloses a dilator to facilitate endoscope insertion into the body. FIG. 1 discloses a dilator with telescoping tubes 3 through 10 adapted to be slid along a wire 1. Storz is relevant only in that it discloses a device which when used in conjunction with a wire guide dilates the puncture site. The Storz disclosure is typical of the devices presently used for dilation of the renal tissue as previously described.

Johnson discloses a combined dilator and catheter. FIG. 6 discloses a surgical instrument with longitudinal channels or grooves 12 in the meeting of jaws 4 to form a longitudinal passage. Johnson also discloses notches in flow communication with longitudinal passes for discharge of secretion, however it is believed that the relevancy ends at that point. Johnson is substantially different in its disclosure as compared to the invention disclosed in this application because the invention disclosed in this application uses a wire guide to guide it to the site at which enlargement is accomplished. The Johnson device, on the other hand, is a combined dilator and catheter which is used to dilate and position a catheter in place.

Although the foregoing references disclose a variety of surgical instruments, it is to be noted that none reveal a surgical instrument with groves in the meeting faces of the jaws and side ports to allow for the instrument to be slidably engaged with a wire guide and inserted into a puncture in renal tissue and then through opening and closing of the handles to tear a hole of sufficient diameter in the tissue for insertion of other instruments. The method disclosed in this application is beneficial in that it helps to alleviate the discomfort to the patient and danger of damage to the surrounding tissue that plague other devices and methods for dilation of renal tissue.

SUMMARY OF THE INVENTION

One embodiment of the device which may be used with this invention for dilating a puncture site in renal tissue according to this invention might include a first member and a second member with a pivot joining these members for a scissor-like motion relative to one another. Each of these members includes a handle portion on one side of the pivot and a wire guide holding portion on the other. The pivot axis is normal to a plane of relative rotation in which the members make their relative motions.

A flat surface is provided on the wire guide holding portion of the first member and the second member. These surfaces extend along the lengths of their respective wire guide holing portions. A groove is located in the flat surface of the wire guide holding portion of the first member and second member. The groove extends longitudinally from one end of the device to the point adjacent the pivot. At the point adjacent to the pivot, the groove exits through the side of the member. When the first member and the second member are caused to contact each other all along the flat surface, a wire guide holding channel is formed with a end hole at one end for introduction of a wire wide and a side port exit for the wire guide near the pivot. First member and second member have triangular cross-sections to provide for better tearing. Also a lock means is provided for holding the members is an adjusted position relative to each other.

One embodiment of the method of this invention for dilating a puncture site in renal tissue according to this invention comprises the steps of inserting a wire guide into a puncture site in the renal tissue, introducing the wire guide through an end hole in a scissor-type renal tissue dilator, inserting the scissor-type renal tissue dilator into the puncture site in the renal tissue, opening the jaws of the scissor-type renal tissue dilator to spread apart and tear the fascial tissue, rotating the scissor-type renal tissue dilator and repeating the step of opening the jaws to spread apart and tear the tissue until the opening through the fascial material is appropriately enlarged.

A second object of the present invention is to provide an improved method for dilating punctures in renal tissue to allow for insertion of other instruments therein.

A third object of the present invention is to provide a method for dilating a puncture site in renal tissue which reduces the pain caused to the patient and reduces the risk of damage to surrounding tissue.

Related objects and advantages of the present invention will be apparent from the following description.

BRIEF DESCRIPTION OF THE DRAWINGS

FIG. 2 is a side elevation view of the device of FIG. 1 taken from the opposite side of the device and showing it in open position.

FIG. 3 is a side elevation view of the jaws comprising a portion of the device with the device in the position of FIG. 1.

FIG. 4 is a top elevation view of a single jaw comprising a portion of the FIG. 1 device for dilating a puncture site in renal tissue.

FIG. 5 is a cross-sectional view taken along the lines 5—5 of FIG. 3 with the device in the closed position of FIG. 1.

DESCRIPTION OF THE PREFERRED EMBODIMENT

Figure 1:
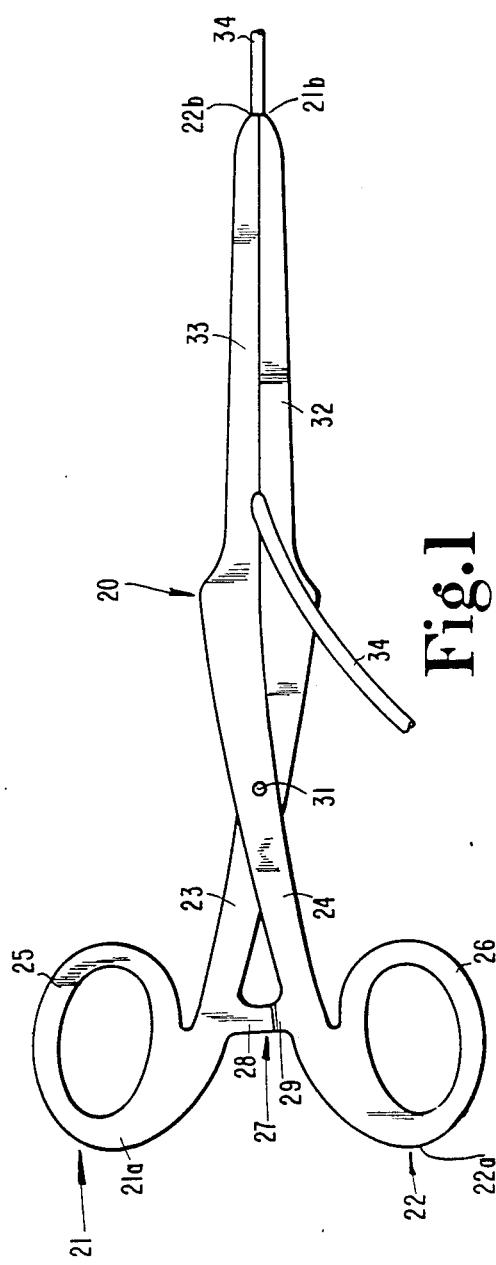
FIG. 1 is a side elevation view of a device for dilating a puncture site in renal tissue according to a typical embodiment of the present invention with the device in closed position.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A renal tissue dilation device 20 which may be used in the method invention is shown in FIG. 1 which includes a first member 21, having a first end 21a and a second end 21b, and a second member 22, having a first end 22a and a second end 22b. These members have respective handle portions 23 and 24 equipped with loops 25 and 26 to receive the finger and thumb. Lock means 27 is provided, the preferred embodiment of which is a ratchet rack 28 on one member and a ratchet catch 29 on the other member. It is immaterial which member carries the rack or the catch. The handles are springy enough that the ratchet rack and catch can readily be separated. When the handles are brought toward each other, the catch snaps along the rack and remains engaged to one of the teeth 30 (FIG. 2). A pivot 31 joins the members together for relative rotation in the planes of FIGS. 1 and 2. The axis of pivot 31 is normal to the plane of FIGS. 1 and 2.

First member 21 and second member 22 include wire guide holding portions 32 and 33 respectively, which receive wire guide 34. Wire guide holding portions 32 and 33 are located on the opposite side of pivot 31 from handles 23 and 24. It is obvious that moving loops 25 and 26 toward each other will move wire guide holding portions 32 and 33 toward each other, while moving loops 25 and 26 away from each other will move wire guide holding portions 32 and 33 away from each other.

Referring more particularly to FIGS. 3–6, there are illustrated the wire guide holding portions 32 and 33. Wire guide holding portion 32 (FIG. 4) will now be more particularly described with the understanding that wire guide holding portion 33 is a mirror image of wire guide holding portion 32. Wire guide holding portion 32 is the elongated and tapering portion of first member 21 which extends from pivot 31 to second end 21b. Wire guide holding portion 32 has longitudinal axis 37. There is a flat surface 38 on wire guide holding portion 32 which is positioned on the side of the wire guide holding portion which is in contact with wire guide holding portion 33 when the device is in the position of FIG. 1. This flat surface 38 extends essentially from pivot 31 to second end 21b. A wire guide receiving means 40 is defined by a groove 41 of semi-circular cross section in the flat surface 38 of wire guide holding portion 32. Groove 41 is symmetrical about longitudinal axis 37 for a substantial distance from end 21b. At a point between second end 21b and pivot 31 groove 41 curves to exit through the side of wire guide holding portion 32. At the point where groove 31 meets end 21b there is formed a wire guide introduction means 43. At the point where groove 41 exists through the side of wire guide holding portion 32 a wire guide exit means 44 is formed. In the illustrated embodiment, the means 43 and 44 respectively consist of the mouths of the grooves 41 at the opposite ends thereof. Since groove 41 is generally semi-cylindrical then wire guide introduction means 43 consists of a semi-circular opening. However, wire guide exit means 44 consists of a semi-eliptical opening since semi-cylindrical groove 41 forms an acute, rather than right, angle with the side of wire guide holding portion 32.

FIG. 5 illustrates that wire guide holding portion 32 has a generally triangular cross section 45. The triangular cross section 45 aids in the tearing of tissue when the renal tissue dilation device 20 is inserted and expanded in a puncture in the renal tissue. In the preferred embodiment of a device to be used in the invention the cross sectional configuration of the closed portions 32 and 33 as illustrated in FIG. 5 is square with two of the four sides perpendicular to the other two and corners 51 having a radius of 1/32".

FIGS. 3 and 5 illustrate the relative location of wire guide holding portions 32 and 33 in closed position. As wire guide holding portions 32 and 33 are mirror images of one another, reference will be made to the parts and part members previously used in describing wire guide holding portion 32 with the understanding that the corresponding structure in wire guide holding portion 33 is also being referred to. Wire guide holding portions 32 and 33 are located relative to one another so that when renal tissue dilation device 20 is in a closed position, flat surfaces 38 contact one another along the full length of the wire guide holding portions. Semi-cylindrical grooves 41 are thus located opposite to one another and therefore form a cylindrical channel 47 which is designed to slidably receive wire guide 34 (FIG. 1). Channel 47 forms an end hole 48 at second ends 21b and 22b. End hole 48 consists of the semi-circular openings of wire guide introduction means 43. A side port 49 consists of wire guide exit means 44. Channel 47 provides flow communication between side port 49 and end hole 48 so that wire guide 34 may be introduced through end hole 48 and slide through channel 47 and exit through side port 49. FIG. 3 also illustrates the wire guide holding portions 32 and 33 are tapered. Wire guide holding portions 32 and 33 taper gradually from a point near pivot 31 toward longitudinal axis 50. As is illustrated in FIG. 3 the taper increases near second ends 22b and 21b so that the renal tissue dilation device 20 has a tapered tip. This tapered tip is provided to offer easy insertion of the renal tissue dilation device 20 into a puncture site in the renal tissue. In one specific embodiment of a device to be used in the invention, the diameter of the unit 0.5"±0.062" from the tip is 0.190"±0.015".

The best mode of practicing a process for dilating a puncture site in a renal tissue consists of several steps. The process involves making a puncture in the renal tissue by means of needle. The wire guide is then threaded through the needle into the kidney. The needle is then removed by sliding it over the wire guide. After the wire guide is inserted in the renal tissue, a modified long-nosed clamp similar to that described above with a means for slidably receiving a wire guide is inserted over the wire guide. The modified long-nosed clamp is slid along the wire guide until the tip of the clamp is through the tissue. After the tip of the clamp is through the tissue, the jaws of the clamp are opened thereby gently tearing the renal tissue and enlarging the puncture site. Should the puncture site not be sufficiently enlarged by this operation, the clamp may be rotated 90° while still through the tissue, and opened again as previously described. The process of rotating the clamp and opening the jaws to tear the tissue is repeated until a opening of the desired size is created.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A process for dilating a puncture site in tissue to allow for insertion of instruments therein, comprising the steps of:
   inserting a wire guide in a puncture in tissue;
   inserting the wire guide in a clamp having jaws with a channel defined therein for receipt of the wire guide;
   sliding the clamp with the wire guide therein along the wire guide until the jaws of the clamp are through the tissue;
   enlarging the puncture in the tissue by opening the jaws of the clamp.

2. A process for dilating a puncture site as described in claim 1, further comprising the steps of:
   rotating the clamp that has its jaws inserted through the enlarged puncture; and then
   further enlarging the puncture by again opening the jaws of the clamp.

3. A process for dilating a puncture site as described in claim 2, further comprising repeating the steps of claim 9 until the puncture is appropriately enlarged.

4. A process for dilating a puncture site in tissue to allow for insertion of instruments therein, as described in claim 3, additionally comprising the step of inserting a needle to form the puncture in the tissue.

5. A process for dilating a puncture site in tissue to allow for insertion of instruments therein, comprising the steps of:
   sliding a clamp having jaws with a channel defined therein for receipt of the wire guide along a wire guide inserted in a puncture in tissue until the jaws are within the puncture; and,
   enlarging the puncture by opening the jaws.

6. A process for dilating a puncture site in tissue to allow for insertion of instruments therein, as described in claim 5, additionally comprising the steps of:
   puncturing the tissue with a needle to define the puncture; and,
   inserting a wire guide in the puncture.

7. A process for dilating a puncture site in tissue to allow for insertion of instruments therein, as described in claim 5, further comprising the step of inserting the wire guide in the clamp prior to said sliding step.

8. A process for dilating a puncture site in tissue to allow for insertion of instruments therein, as described in claim 7, further comprising the steps of:

rotating the clamp that has its jaws inserted through the enlarged puncture; and then further enlarging the puncture by again opening the jaws of the clamp.

9. A process for dilating a puncture site, as described in claim 8, further comprising repeating the steps of claim 8 until the puncture is appropriately enlarged.

* * * * *